US008239004B2

(12) United States Patent
Mackiewicz

(10) Patent No.: US 8,239,004 B2
(45) Date of Patent: Aug. 7, 2012

(54) METHODS FOR IMAGING AN IMPLANT SITE

(75) Inventor: David Mackiewicz, Scotts Valley, CA (US)

(73) Assignee: Abbott Laboratories, Abbott Park, IL (US)

( * ) Notice: Subject to any disclaimer, the term of this patent is extended or adjusted under 35 U.S.C. 154(b) by 491 days.

(21) Appl. No.: 12/482,343

(22) Filed: Jun. 10, 2009

(65) Prior Publication Data

US 2010/0152572 A1 Jun. 17, 2010

Related U.S. Application Data

(60) Provisional application No. 61/138,448, filed on Dec. 17, 2008.

(51) Int. Cl.
*A61B 6/00* (2006.01)
(52) U.S. Cl. ....................................................... 600/424
(58) Field of Classification Search .................. 600/117, 600/424, 587; 382/128, 130–132; 378/163, 378/205–207
See application file for complete search history.

(56) References Cited

U.S. PATENT DOCUMENTS

| 3,812,842 | A | * | 5/1974 | Rodriguez | 600/436 |
| 4,915,112 | A | * | 4/1990 | Singer | 600/426 |
| 5,095,911 | A | * | 3/1992 | Pomeranz | 600/463 |
| 5,192,302 | A | | 3/1993 | Kensey et al. | |
| 5,222,974 | A | | 6/1993 | Kensey et al. | |
| 5,304,184 | A | | 4/1994 | Hathaway et al. | |
| 5,419,324 | A | * | 5/1995 | Dillow | 600/426 |
| 5,674,231 | A | | 10/1997 | Green et al. | |
| 5,676,689 | A | | 10/1997 | Kensey et al. | |
| 5,860,923 | A | * | 1/1999 | Lenker et al. | 600/433 |
| 5,910,154 | A | * | 6/1999 | Tsugita et al. | 606/200 |
| 5,970,119 | A | * | 10/1999 | Hofmann | 378/163 |
| 6,078,832 | A | * | 6/2000 | Lenker et al. | 600/433 |
| 6,097,978 | A | * | 8/2000 | Demarais et al. | 600/429 |
| 6,142,987 | A | * | 11/2000 | Tsugita | 604/500 |
| 6,197,042 | B1 | | 3/2001 | Ginn et al. | |
| 6,344,044 | B1 | | 2/2002 | Fulkerson et al. | |
| 6,391,048 | B1 | | 5/2002 | Ginn et al. | |
| 6,450,976 | B2 | * | 9/2002 | Korotko et al. | 600/587 |
| 6,461,364 | B1 | | 10/2002 | Ginn et al. | |
| 6,623,510 | B2 | | 9/2003 | Carley et al. | |
| 6,719,777 | B2 | | 4/2004 | Ginn et al. | |
| 7,054,476 | B2 | * | 5/2006 | Oosawa et al. | 382/132 |
| 7,211,101 | B2 | | 5/2007 | Carley et al. | |
| 7,670,369 | B2 | * | 3/2010 | Schaeffer | 623/1.31 |
| 7,697,972 | B2 | * | 4/2010 | Verard et al. | 600/424 |
| 2004/0153122 | A1 | | 8/2004 | Palermo | |
| 2006/0025681 | A1 | * | 2/2006 | Abovitz et al. | 600/425 |
| 2008/0009933 | A1 | | 1/2008 | Ta et al. | |
| 2008/0063304 | A1 | * | 3/2008 | Russak et al. | 382/298 |
| 2009/0156929 | A1 | | 6/2009 | Franco | |
| 2011/0034802 | A1 | | 2/2011 | Shrivastava et al. | |

OTHER PUBLICATIONS

U.S. Appl. No. 61/138,448, filed Dec. 17, 2008, Mackiewicz.
U.S. Appl. No. 61/014,395, filed Dec. 17, 2007, Franco.
U.S. Appl. No. 12/328,468, filed Jun. 10, 2011, Office Action.
U.S. Appl. No. 12/328,468, mailed Apr. 27, 2012, Office Action.

* cited by examiner

*Primary Examiner* — Francis Jaworski
(74) *Attorney, Agent, or Firm* — Workman Nydegger; Jonathan Feuchtwang

(57) ABSTRACT

A method for preparation of an implant site is disclosed. The method includes positioning a patient relative to an imaging device. A first image of the implant site may be obtained. A distance from an access location to a deployment location may be determined. Other images may be obtained to determine the distance from the access location to the deployment location.

18 Claims, 8 Drawing Sheets

METHODS FOR IMAGING AN IMPLANT SITE

CROSS-REFERENCE TO RELATED APPLICATIONS

This U.S. patent application claims the benefit of and priority to U.S. Provisional Patent Application having Ser. No. 61/138,448, filed on Dec. 17, 2008, the disclosure of which is incorporated herein by reference in its entirety. This application also incorporates the disclosure of Ser. No. 10/616,125, filed Jul. 8, 2003 by reference in its entirety.

FIELD OF THE INVENTION

The present invention relates generally to medical devices. More particularly the present invention relates to methods for imaging an implant site.

BACKGROUND OF THE INVENTION

Vein thrombosis is a medical condition wherein a blood clot, or thrombus, has formed inside a vein. Such a clot often develops in the calves, legs, or lower abdomen, but can also affect other veins in the body. The clot may partially or completely block blood flow, and may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury. However, there are many other situations that cause the formation of a blood clot.

Vein thrombosis is a serious problem because of the danger that the clot may break off and travel through the bloodstream to the lungs, causing a pulmonary embolism. This is similar to a blockage of the blood supply to the lungs that causes severe hypoxia and cardiac failure, and frequently results in death. For many patients, anti-coagulant drug therapies may be sufficient to dissipate the clots. For example, patients may be treated with anticoagulants such as heparin and with thrombolytic agents such as streptokinase.

Unfortunately, some patients may not respond to such drug therapy or may not tolerate such therapy. Also, there may be other reasons why an anticoagulant is not desirable. For example, patients may have an acute sensitivity to heparin or may suffer from prolonged internal and/or external bleeding as a result of such drug therapies. Also, such drug therapies simply may be ineffective in preventing recurrent pulmonary emboli. In such circumstances, surgical procedures are required to prevent pulmonary emboli. Methods for prevention of primary or recurrent pulmonary emboli when anticoagulation therapies are ineffective are well-defined in the prior art. The current standard of therapy for prevention of pulmonary emboli in patients who are classified high-risk or are unable to be anticoagulated is percutaneous insertion and placement of an inferior vena cava filter device.

Additionally, a pulmonary embolism is an obstruction of the pulmonary artery or one of its branches by a blood clot or other foreign substance. A pulmonary embolism can be caused by a blood clot which migrated into the pulmonary artery or one of its branches. Mechanical interruption of the inferior vena cava typically presents an effective method of preventing of pulmonary embolisms.

Vena cava filters are devices which are implanted in the inferior vena cava, providing a mechanical barrier to undesirable particulates. The filters may be used to filter peripheral venous blood clots and other particulates, which if remaining in the blood stream can migrate in the pulmonary artery or one of its branches and cause harm.

Methods for imaging an implant site may be useful. Furthermore, methods for delivering an implantable device may also be useful.

BRIEF SUMMARY

An embodiment of a method for delivering an implantable device to an implant site is described. The method includes positioning a patient relative to an imaging device. A first image of the implant site is obtained. A distance from an access location to a deployment location is determined. A delivery device is inserted from the access location the determined distance. The implantable device is deployed.

An embodiment of a method for preparation of an implant site for an implantable device is disclosed. The method may include positioning a patient relative to an imaging device. A first image of the implant site may be obtained. A distance from an access location to a deployment location is determined.

An embodiment of method for delivering a lumen filter to an implant site is described. The method includes positioning a patient relative to a lumen filter. A first image of the implant site is obtained using computed radiography. A second image of the implant site is obtained using computed radiography. A distance from an access location to a deployment location is determined. The distance determination includes measuring a first distance from the first image, measuring a second distance from the second image, and determining an approximate total distance from the access location to the deployment location using the first distance and the second distance. A delivery device is inserted from the access location the determined distance. The lumen filter is deployed.

In some embodiments, the delivery device includes at least one distance mark. In further embodiments, the determined distance is indicated by the at least one distance mark.

The location of the implantable device, in some embodiments, is verified. In further embodiments, the location of the implantable device is verified using fluoroscopy. In still further embodiments, the location of the implantable device is verified using ultrasonic imaging.

In some embodiments, the delivery device is a catheter. In further embodiments, determining a distance from an access location to a deployment location is performed by a computing device.

A second image of the implant site, in some embodiments, may be obtained. In further embodiments, a plane of the first image and a plane of the second image are separated by an angle. In still further embodiments, the plane of the first image and the plane of the second image are parallel to a vertical axis through a patient.

In some embodiments, determining the distance from an access location to a deployment location includes measuring a first distance from the first image and determining an approximate total distance from the access location to the deployment location using the first distance. In further embodiments, determining the distance from an access location to a deployment location includes measuring a first distance from the first image, measuring a second distance from the second image, and determining an approximate total distance from the access location to the deployment location using the first distance and the second distance. In still further embodiments, the approximate total distance is accurate within about one inch.

A third image of the implant site, in some embodiments, is obtained. In further embodiments, a plane of the first image and a plane of the second image are separated by a first angle and the plane of the first image and a plane of the third image are separated by a second angle. In further embodiments, the first image is obtained using projectional radiography. In still further embodiments, the implantable device is a vena cava filter.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

Figures 1, 2:
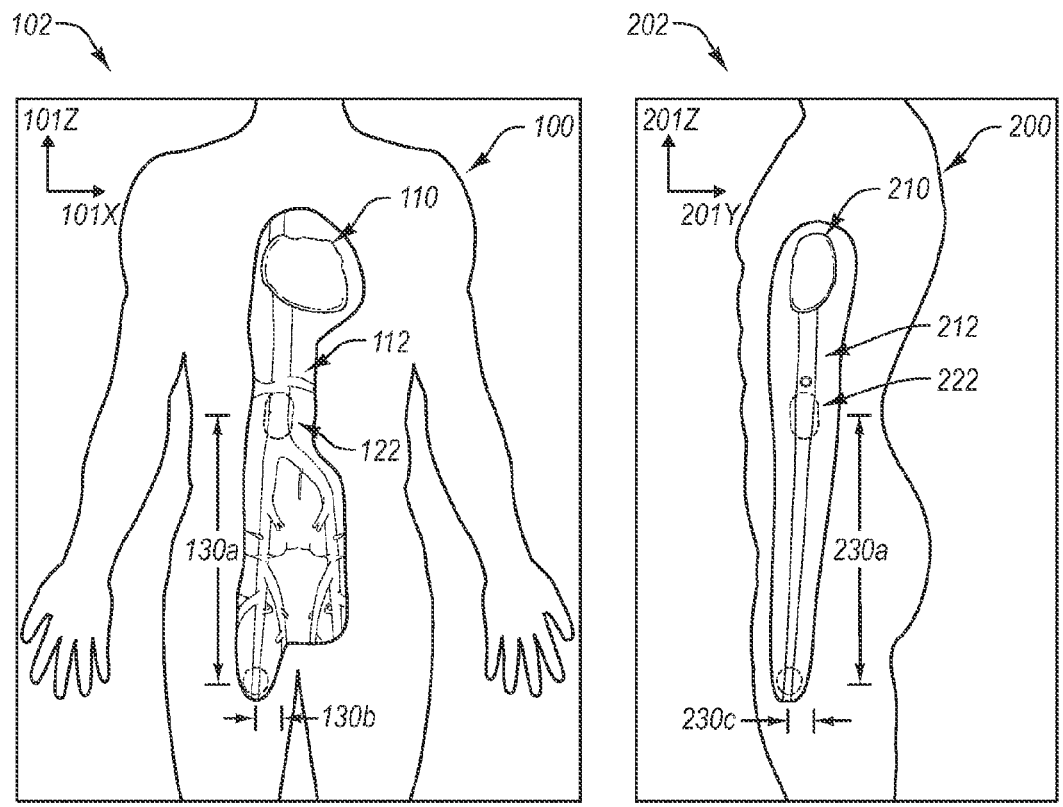
FIG. 1 illustrates an embodiment of an image of an implant site.
FIG. 2 illustrates another embodiment of an image of an implant site.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The embodiments described herein extend generally to methods for imaging an implant site. By way of example only, a delivery system may include a delivery device and an implantable device. For instance, embodiments of implantable devices, such as implantable filters (e.g. including vena cava and/or other lumen filters), closure elements, and stents and delivery apparatus, such as delivery catheters, closure element apparatus, and stent delivery apparatus, are described.

A fluoroscope may be used to deliver an implantable device, such as a vena cava filter. The fluoroscope may allow a technician to monitor the location of the implantable device within the patient. This may facilitate delivery of the implantable device at the appropriate location.

However, it may be desirable to facilitate placement of implantable devices without the use of a fluoroscope. For example, some intensive care units and/or emergency rooms are not equipped with a fluoroscope. Other imaging devices (x-ray imaging devices, such as x-ray radiographs, and/or ultrasonic imaging devices) may be more readily accessible.

Non-fluoroscopic imaging devices may be used to determine the appropriate location of the implantable device. For example, a non-fluoroscopic imaging device may be used to determine a distance from an access location to a desired deployment location.

A delivery system may incorporate a measuring scale and/or the determined distance to locate the implantable device. Once the patient is stabilized, the location of the implantable device may be verified using fluoroscopic, ultrasonic, and/or other methods.

FIG. 1 illustrates an embodiment of an image 102 of an implant site 100 associated with methods for imaging an implant site for facilitating delivery of an implantable device. The image 102 shown in FIG. 1 may be a partial image taken from the front of a patient. For example, the image may be an antero-posterior projection. In other embodiments, the image 102 may be taken from other perspectives and/or references. For instance, other projections may be used, such as, a postero-anterior, lateral, oblique, flexion, extension, horizontal beam lateral, horizontal central ray, prone, supine, decubitus, caudal, and/or other projections. FIG. 1 illustrates the patient's heart 110 and inferior vena cava 112. In another instance, other portions of the patient's vasculature may be included, such as the superior vena cava, pulmonary artery, pulmonary vein, other vasculature, and/or combinations thereof.

Discussion will be made relative to deploying a vena cava filter in the vena cava. However, the techniques, apparatus, and method described herein may be used for other procedures, such as, but not limited to implanting a filter to capture and/or lyse arterial thrombosis.

The image 102 may include an implant site 100 that may include an access location 142 and a deployment location 144, other locations, and/or combinations thereof. The access location 142 may be the location where an implantable device may be inserted into a patient. The access location 142 shown in FIG. 1 may be through the femoral vein. In other embodiments, other access locations may be used. For example, the interior jugular vein, basilic vein, and/or other vascular access locations.

The deployment location 144 may be the location where the implantable device may be deployed. In the present embodiment, the deployment location 144 may include an area below the inferior vena cava and the lowest renal vein. In other embodiments, the deployment location 144 may include other locations.

The image 102 may be a two-dimensional image oriented about at least two axes 101x, 101z. In other embodiments, the image may be three-dimensional. The axes 101x, 101z, in the present embodiment, include an x-axis 101x and a z-axis 101z. The x-axis 101x may be a lateral axis. The z-axis 101z may be a longitudinal axis. Other axes may be used. Reference to certain axes in now way limits applicability of the invention to other orientations and axes.

The image 102 may indicate a first distance 130a from the access location 142 to the deployment location 144. The first distance 130a may be an approximate vertical (i.e. longitudinal) distance. For instance, the first distance 130a may be an approximate distance from the access location 142 to the deployment location 144 in the direction of the z-axis 101z.

The image 102 may include a second distance 130b from the access location 142 to the deployment location 144. The second distance 130b may be an approximate horizontal (i.e. lateral) distance. For instance, the second distance 130b may be an approximate distance from the access location 142 to the deployment location 144 in the direction of the x-axis 101x. The image 102 may include further dimensions, such as a linear distance from the access location 142 to the deployment location 144, an approximate distance (i.e. the approximate actual distance from the access location 142 to the deployment location 144), other dimensions, and/or combinations of dimensions. Approximate distances may be accurate in some embodiments, within about one inch.

FIG. 2 illustrates another embodiment of an image 202 of an implant site 200. The image 202 shown in FIG. 2 may be a partial image taken from a side of a patient. For example, the image may be a lateral projection. The elements of the image 202 of this other embodiment may be functionally similar to the elements of the image 102 previously described above and shown in FIG. 1 in most respects, wherein certain features will not be described in relation to this embodiment wherein those components may function in the manner as described above and are hereby incorporated into this alternative embodiment described below. Like structures and/or components are given like reference numerals.

The image 202 may include at least a portion of the patient's vasculature. The image 202 may include an implant site 200 that may include an access location 242 and a deployment location 244. The access location 242 shown in FIG. 2 may be through the femoral vein. In the present embodiment, the deployment location 244 may include an area below the inferior vena cava and the lowest renal vein.

The image 202 may be a two-dimensional image oriented about at least two axes 201y, 201z. The axes 201y, 201z, in the present embodiment, include a y-axis 201y and a z-axis 201z. The y-axis 201y may be a lateral (i.e. depth) axis. The z-axis 201z may be a longitudinal (i.e. height) axis. Other axes may be used. Reference to certain axes in now way limits applicability of the invention to other orientations and axes.

The image 202 may indicate a first distance 230a from the access location 242 to the deployment location 244. The first distance 230a may be an approximate vertical (i.e. longitudinal) distance. For instance, the first distance 230a may be an approximate distance from the access location 242 to the deployment location 244 in the direction of the z-axis 201z.

The image 202 may include a third distance 230c from the access location 242 to the deployment location 244. The third distance 230c may be an approximate depth (i.e. lateral) distance. For instance, the third distance 230c may be an approximate distance from the access location 242 to the deployment location 244 in the direction of the y-axis 201y.

Figure 3:
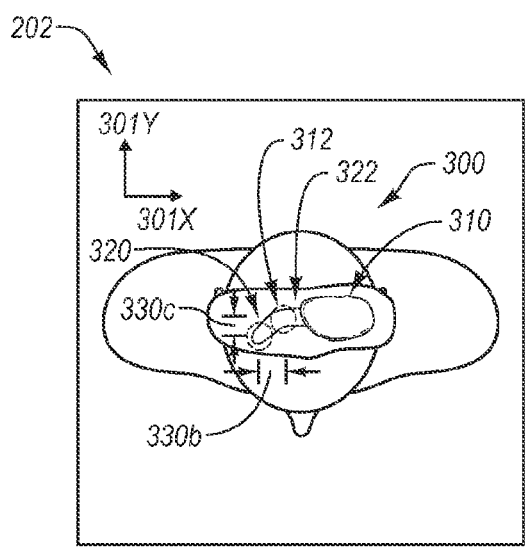
FIG. 3 illustrates a further embodiment of an image of an implant site.

FIG. 3 illustrates a further embodiment of an image 302 of an implant site 300. The image 302 shown in FIG. 3 may be a partial image taken from the top of a patient. For example, the image may be a cranial projection. The elements of the image 302 of this other embodiment may be functionally similar to the elements of the images 102, 202 previously described above and shown in FIGS. 1 and 2 in most respects, wherein certain features will not be described in relation to this embodiment wherein those components may function in the manner as described above and are hereby incorporated into this alternative embodiment described below. Like structures and/or components are given like reference numerals.

The image 302 may include at least a portion of the patient's vasculature. The image 302 may include an implant site 300 that may include an access location 342 and a deployment location 344. The access location 342 shown in FIG. 3 may be through the femoral vein. In the present embodiment, the deployment location 344 may include an area below the inferior vena cava and the lowest renal vein.

The image 302 may be a two-dimensional image oriented about at least two axes 301x, 301y. The axes 301x, 301y, in the present embodiment, include an x-axis 301x and a y-axis 301y. The x-axis 301x may be a width (i.e. lateral) axis. The y-axis 301y may be a depth (i.e. lateral) axis. Other axes may be used. Reference to certain axes in now way limits applicability of the invention to other orientations and axes.

The image 302 may include a second distance 330b from the access location 342 to the deployment location 344. The second distance 330b may be an approximate horizontal (i.e. lateral) distance. For instance, the second distance 330b may be an approximate distance from the access location 342 to the deployment location 344 in the direction of the x-axis 301x.

The image 302 may include a third distance 330c from the access location 342 to the deployment location 344. The third distance 330c may be an approximate depth (i.e. lateral) distance. For instance, the third distance 330c may be an approximate distance from the access location 342 to the deployment location 344 in the direction of the y-axis 301y.

Figure 4:
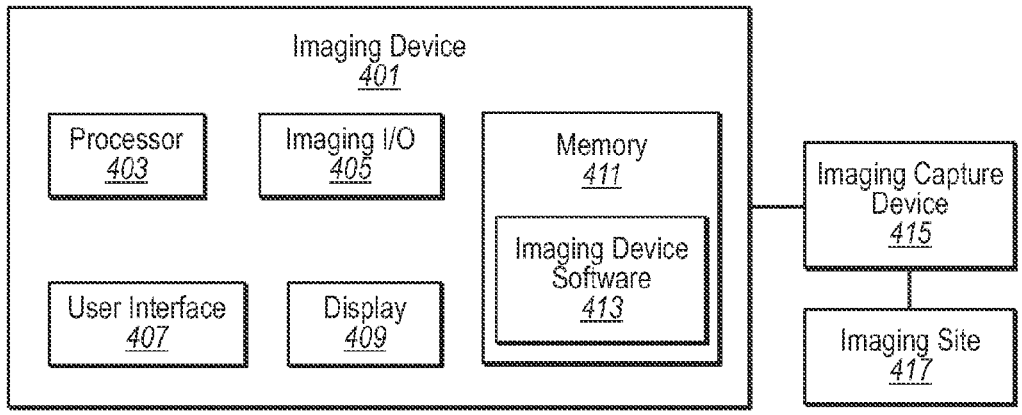
FIG. 4 illustrates an embodiment of an imaging device.

FIG. 4 illustrates a schematic representation of an imaging device 401. The imaging device 401 can generate an image of an implant site, such as the implant sites 100, 200, 300 described above in connection with the description of FIGS. 1-3. The imaging device 401 may include an x-ray imaging device, an ultrasonic imaging device, and/or other imaging devices. The imaging device 401 may take static images. For example, the imaging device 401 may use projectional radiography. In some embodiments, the imaging device 401 may use direct radiography, computed radiography, or the like. For example, the imaging device 401 may use film, an imaging plate, or the like. In other embodiments, the imaging device 401 may capture dynamic images.

The imaging device 401 may include a processor 403. The processor 403 may be in electronic communication with an imaging I/O 405. The imaging I/O 405 may be in electronic communication with an image capturing device 415, which can take an image of the implant site or any portion thereof. The image capturing device 415 may include a charge coupled device, an ultrasonic sensor, an imaging plate, and/or other image capturing devices. The charge coupled device and/or imaging plate may be configured to generate images such as x-ray images. The ultrasonic sensor may be configured to generate images based on reflected ultrasonic waves.

The processor 403 may be in electronic communication with a user interface 407. The user interface 407 may include a keyboard, mouse, and/or other user interface. The processor 403 may also be in electronic communication with a display 409. The display 409 may be configured to display images generated by the image capturing device. In some embodiments, the imaging device 401 may print the images generated by the image capturing device using a printer or other device rather than or in addition to using a display 409.

Memory 411 may be in electronic communication with the processor 403. The memory 411 may include imaging device software 413. The imaging device software 413 may include instructions executable to perform portions of the functions described below.

FIGS. 5A-5G illustrate various steps in the deployment of an implantable device 500. The implantable device 500 in the present embodiment, may be a lumen filter. In other embodiments, other implantable devices and/or delivery systems may be used.

Figure 5A:
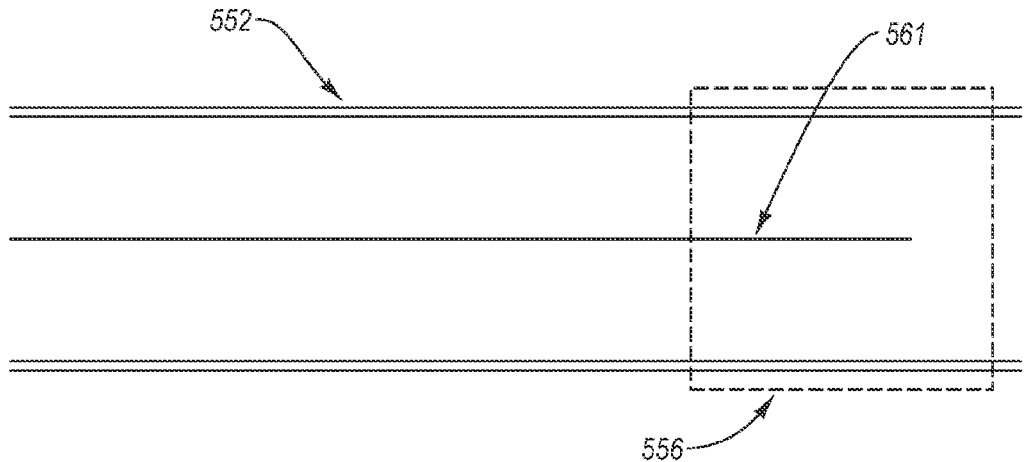
FIGS. 5A-5G illustrate various steps in the deployment of an implantable device 500.

FIG. 5A illustrates a deployment site 556 within a body lumen 552, such as a blood vessel like the vena cava, with a guidewire 561 partially inserted therethrough. The guidewire 561 may be inserted through an access site (shown as 142, 242, 342 in FIGS. 1-3) toward the deployment site 556 (described as a deployment location 144, 244, 344 in FIGS. 1-3).

The guidewire 561 may be used to locate the deployment site 556. In other embodiments, other methods may be used in addition to or instead of a guidewire 561. For example, imaging device 401 may be used to locate the deployment site 556.

Figure 5B:
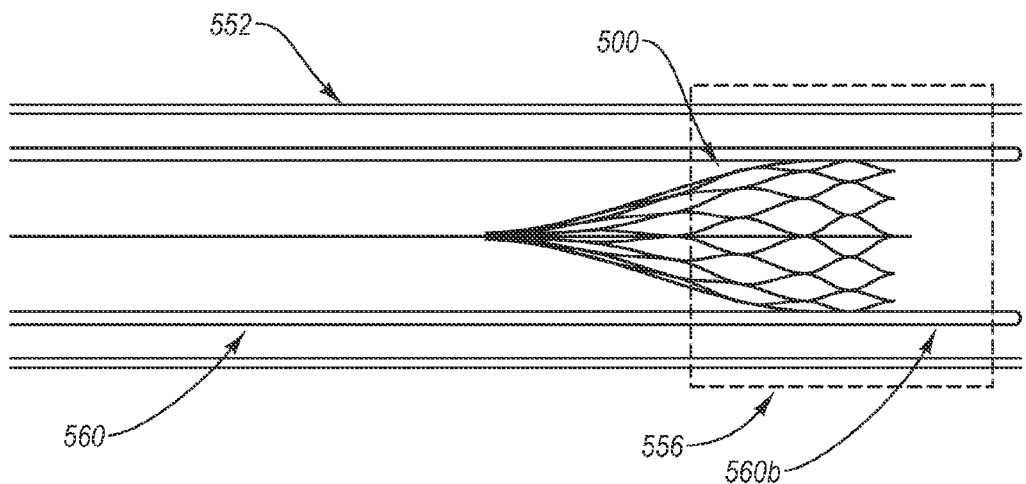

As shown in FIG. 5B, a delivery apparatus 560 may use the guidewire 561 to guide a distal end 560b of the delivery apparatus 560 toward the delivery site 556. An implantable device 500 may be disposed within the delivery apparatus 560. The implantable device 500, in the present embodiment, may be disposed within the delivery apparatus 560 while in a collapsed state. While in the collapsed state, the implantable device 500 may be longitudinally elongated with respect to a deployed state.

The guidewire 561 may be removed after the distal end 560b of the delivery apparatus 560 is located near the delivery site 556. Alternatively, the guidewire 561 may remain.

Figure 5C:
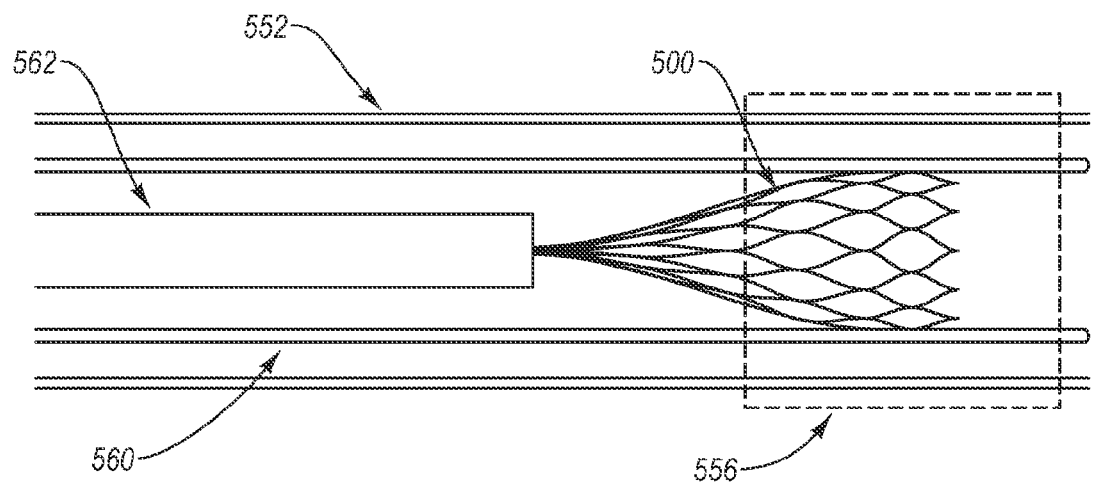

A deployment member 562 may be inserted through the delivery apparatus 560, as shown in FIG. 5C. The deployment member 562 may be used to deploy the implantable device 500. In the embodiment shown in FIG. 5D, the deployment member 562 may urge the implantable device 500 toward the distal end 560b of the delivery apparatus 560 while the delivery apparatus 560 may remain generally stationary.

The deployment member 562 may urge the implantable device 500 by abutting the proximal end 502a of the filter 500. The deployment member 562 may include a receiving area (not shown), such as a convex portion configured and dimensioned to receive the proximal end 502a, to facilitate urging the implantable device 500 out of the delivery apparatus 560.

Figure 5D:
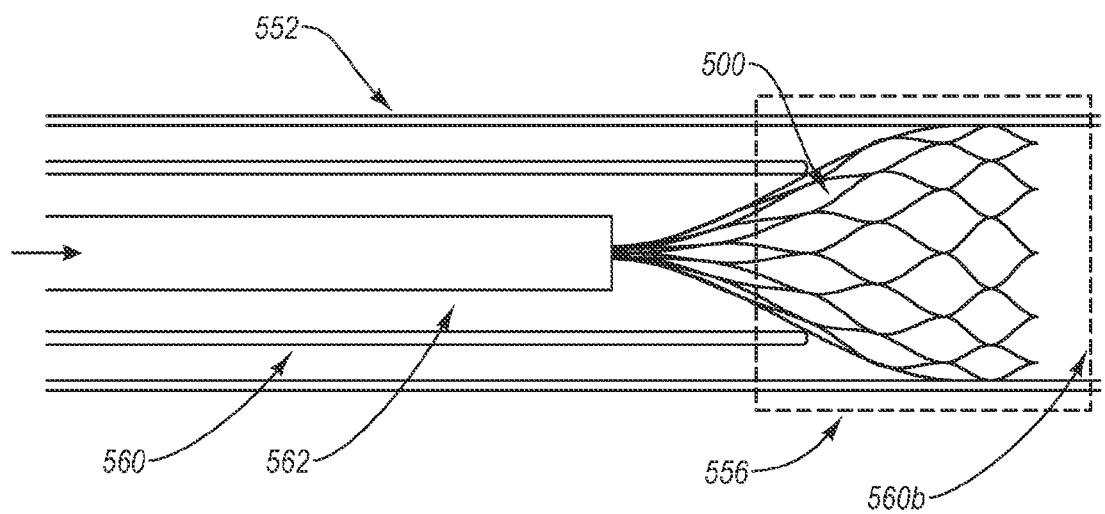
Figure 5D:
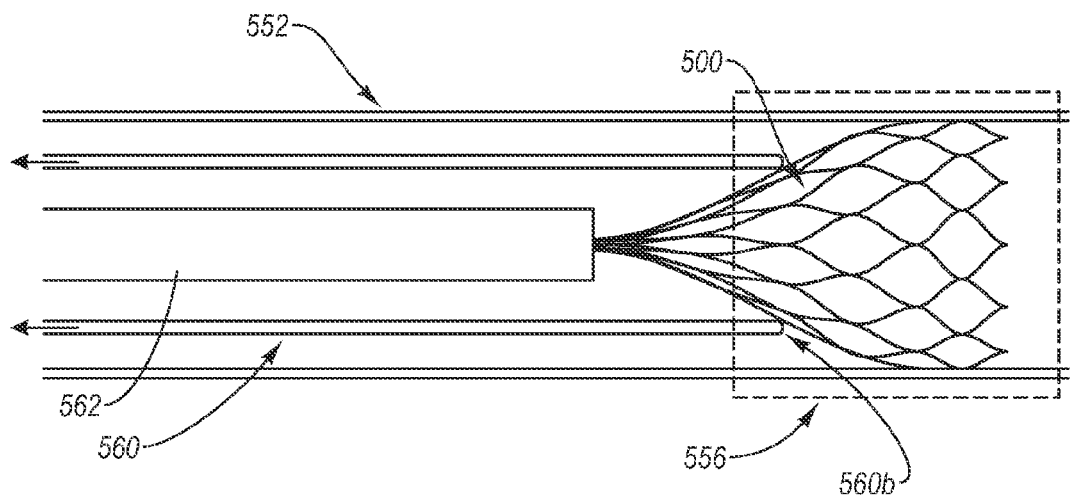

In the embodiment shown in FIG. 5D', the delivery apparatus 560 may be retracted while the deployment member 562 may remain generally stationary. In other embodiments, the delivery apparatus 560 and/or the deployment member 562 may cooperate to facilitate deployment of the implantable device 500. For instance, the delivery apparatus 560 may be retracted while the deployment member 562 may urge the implantable device 500 toward the distal end 560b of the delivery apparatus 560.

Figure 5E:
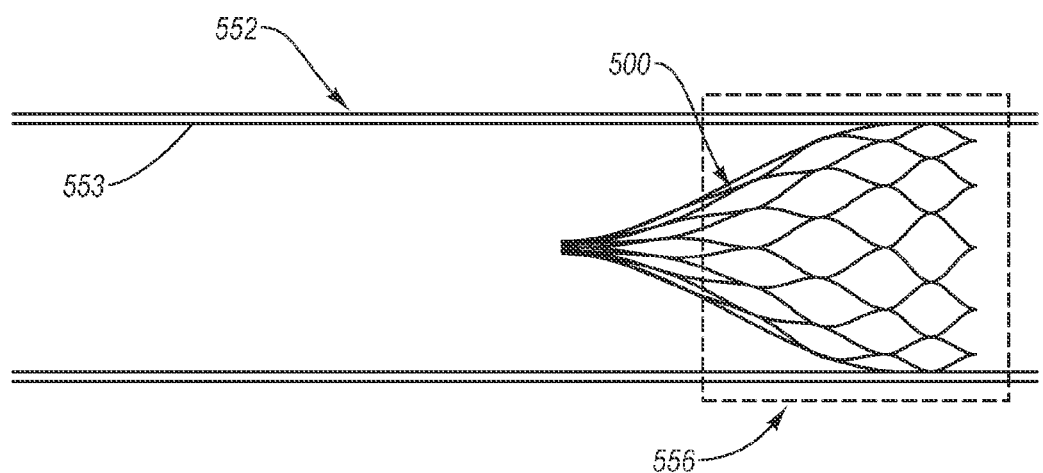

FIG. 5E illustrates a deployed implantable device 500 within the body lumen 552. In the deployed configuration, the implantable filter 500 may engage an inside surface 553 of the body lumen 552. The engaging portion 520 of the implantable lumen filter may engage the inside surface 553 of the body lumen 552. In the deployed configuration, the implantable device 500 may be longitudinally reduced with respect to a collapsed configuration.

Figure 5F:
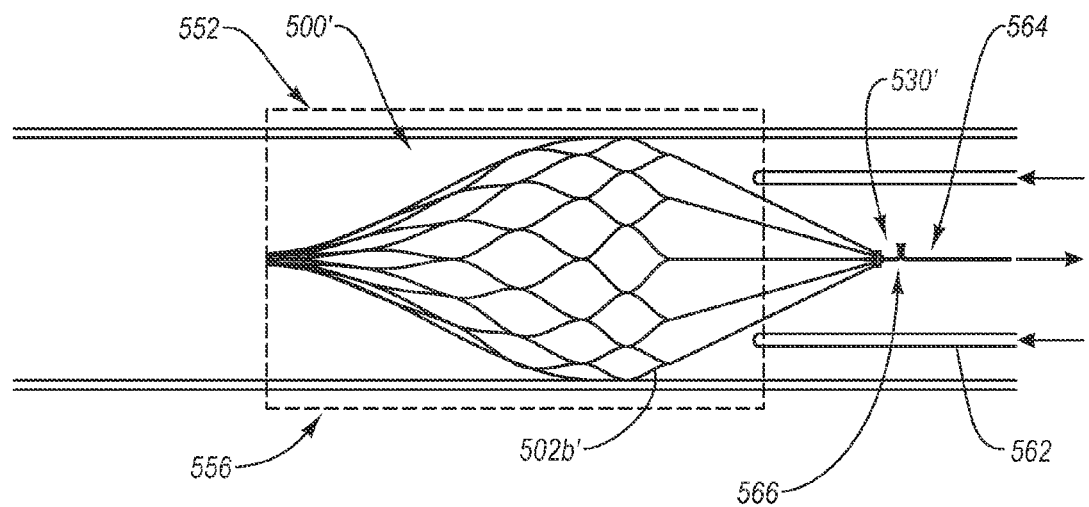
Figure 5F:
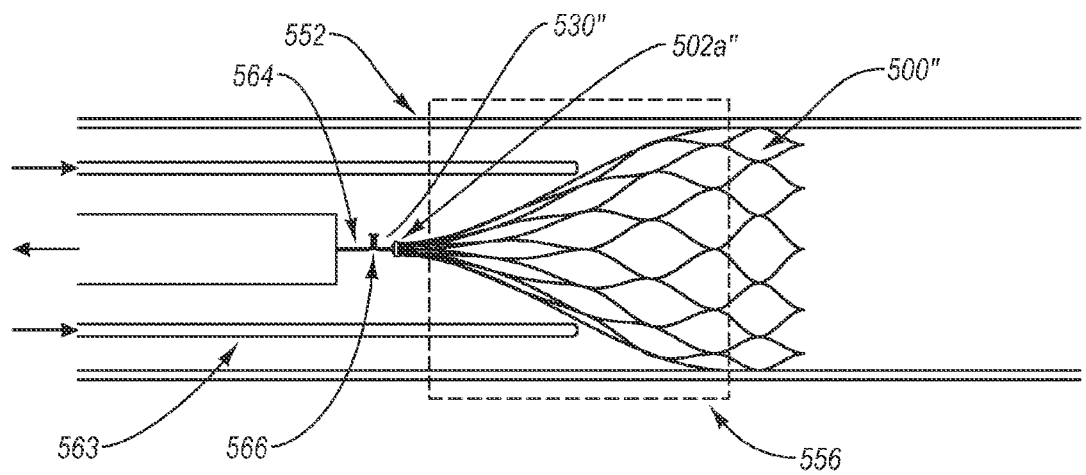
Figure 5G:
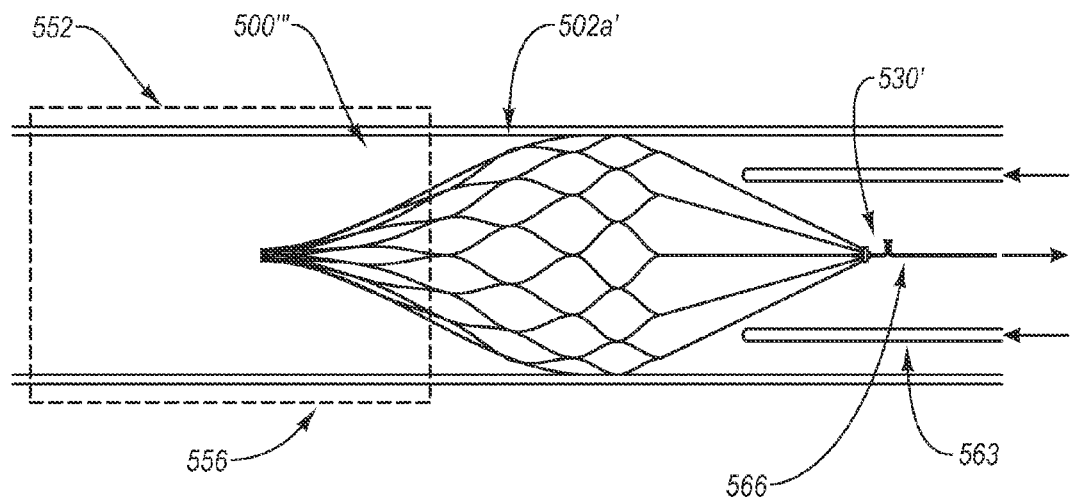
Figure 5G:
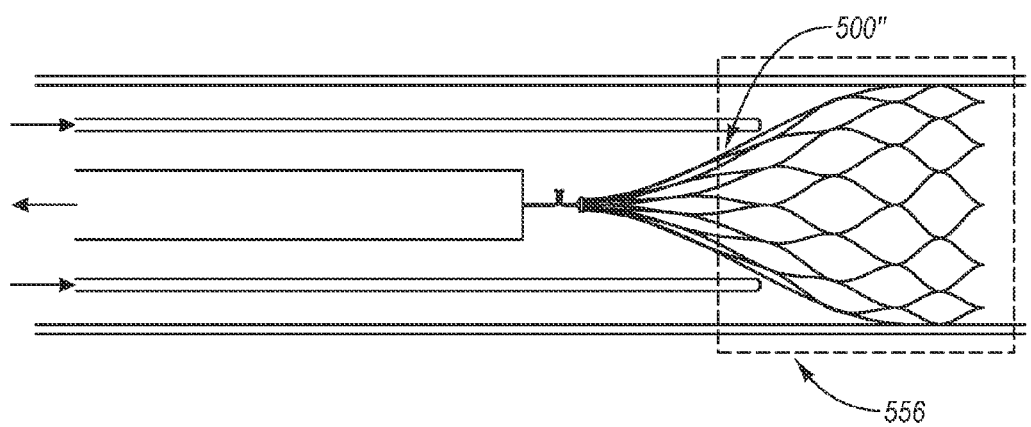

The implantable device 500' shown in FIGS. 5F-5G may include a retrieval portion 530' near the proximal end 502a' of the implantable device 500'. The retrieval portion 530' may be operatively connected to the proximal end 502a of the implantable device 500.

The implantable device 500' may be engaged by a retrieval member 564. The retrieval member 564 may include a retrieving mechanism 566, such as a hook and/or other retaining mechanism, configured to engage the retrieval portion 530'.

Upon engaging the retrieval portion 530', the retrieval member 564 may urge the implantable device 500' into the retrieval apparatus 563. For example, urging the implantable device 500' toward the retrieval apparatus 563 may facilitate disengaging the engagement portion 520.

In the present embodiment, the retrieval apparatus 563 and the retrieval member 564 may both move in generally opposite directions to urge the implantable device 500' into the retrieval apparatus 563 into a compressed state, such that the implantable device 500' may be longitudinally elongated with respect to a deployed state, as shown in FIG. 5G.

The implantable device 500" shown in FIGS. 5F'-5G' is shown with a retrieval portion 530" near the proximal end 502a" of the implantable device 500".

The implantable lumen filters 500" may be engaged by a retrieval member 564. The retrieval member 564 may include a retrieving mechanism 566, such as a hook and/or other retaining mechanism, configured to engage the retrieval portion 530".

Upon engaging the retrieval portion 530", the retrieval member 564 may limit motion away from the retrieval member 564. In the present embodiment, the retrieval member 564 may remain generally stationary while the retrieval apparatus 563 is advanced distally to urge the implantable device 500" into the retrieval apparatus 563. For example, advancing the retrieval apparatus 563 distally may facilitate disengaging the engagement portion 520.

In the present configuration, the retrieval member 564 remains generally stationary while the retrieval apparatus 563 moves to urge the implantable device 500" into the retrieval apparatus 563 into a compressed state, such that the implantable device 500" may be longitudinally elongated with respect to a deployed state, as shown in FIG. 5G'. In other embodiments, both the retrieval apparatus 563 and the retrieval member 564 may move in generally opposite directions.

Figure 6:
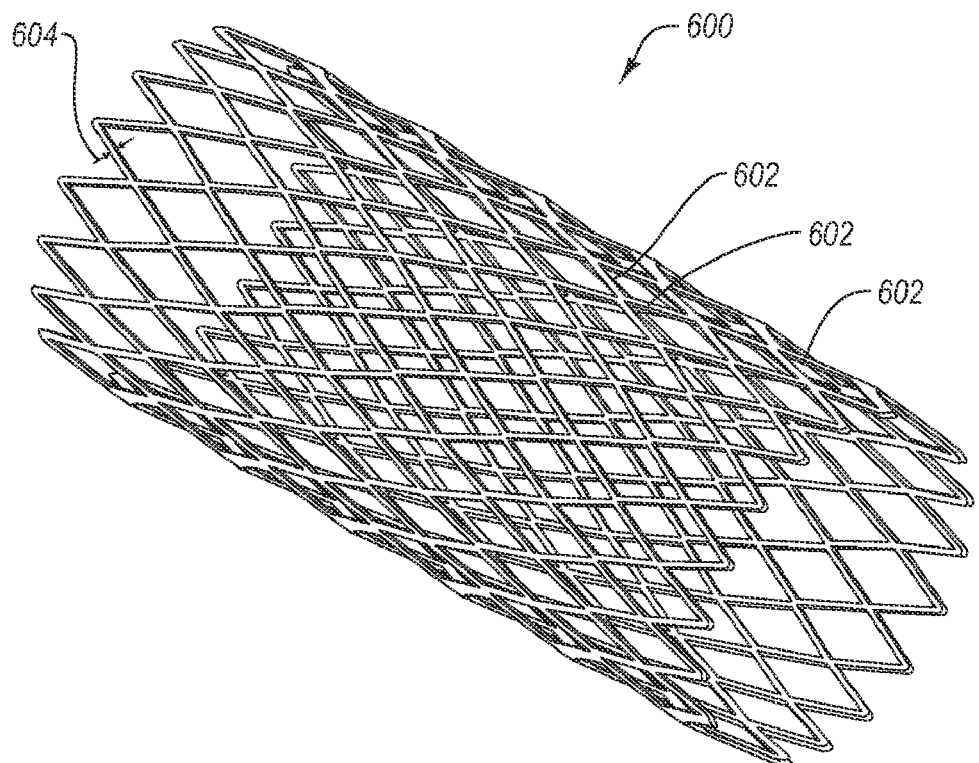
FIG. 6 illustrates another embodiment of an implantable device.

After the implantable devices 500, 500', 500" are within the retrieval apparatus 563, the retrieval apparatus 563 and implantable devices 500, 500', 500" may be withdrawn through an access site (shown as 654a, 654b in FIG. 6).

FIG. 6 illustrates another embodiment of an implantable device 620. The implantable device 620 of the present embodiment may be a stent. The stent may include a structure configured and dimensioned as a stent to be used within a lumen of an animal. An example of a stent is described in U.S. patent application Ser. No. 10/616,125, filed Jul. 8, 2003, and entitled "Drug Eluting Stent and Method of Manufacture," the disclosure of which is hereby incorporated by reference in its entirety.

Figure 7:
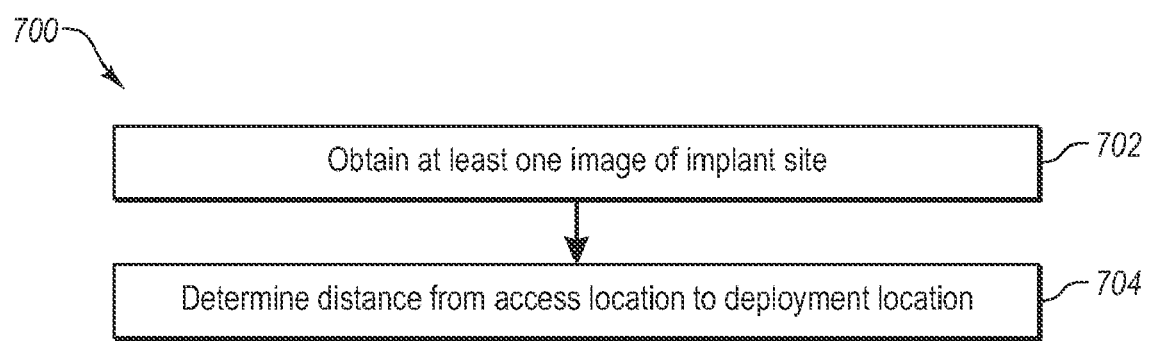
FIG. 7 illustrates an embodiment of a method for imaging an implant site.

FIG. 7 illustrates an embodiment of a method 700 for imaging an implant site. In the present embodiment, the method 700 may be used in conjunction with the imaging device 401 and components described in connection with FIG. 4, the implantable devices 520, 620 described in connection with FIGS. 5-6, and other system components and/or any other systems and/or apparatus for imaging an implantable device described and/or incorporated herein.

The method 700 may include obtaining at least one image of the implant site, as represented by block 702. The first image may be obtained using various imaging devices. The first image may be functionally similar to the images 102, 202, 302 previously described above and shown in FIGS. 1-3 in most respects, wherein certain features will not be described in relation to this embodiment wherein those components may function in the manner as described above and are hereby incorporated into this alternative embodiment described below.

A distance from an access location to a deployment location may be determined, as represented by block 704. The distance may be an approximate distance. The distance may be determined by a technician, an imaging device, and/or other determiners.

For instance, a technician may inspect the first image of the implant site to determine an approximate distance. In another example, the imaging device may interpret data from the first image of the implant site to determine an approximate distance. The determined distance may be used to approximate distance that of a delivery device might travel to deliver an implantable device near a delivery location.

The distance may be determined based on information provided by the first image of the implant site. For instance, a technician may measure the distance from the access location to the deployment site. Measurements may be taken directly (i.e. by measuring the distance along the route of the lumen from the access location to the delivery location), by computations involving a plurality of measurements (i.e. in a frontal image, measuring the vertical distance and the horizontal distance and determining the distance of the hypotenuse), other measuring processes, and/or combinations of the same.

Figure 8:
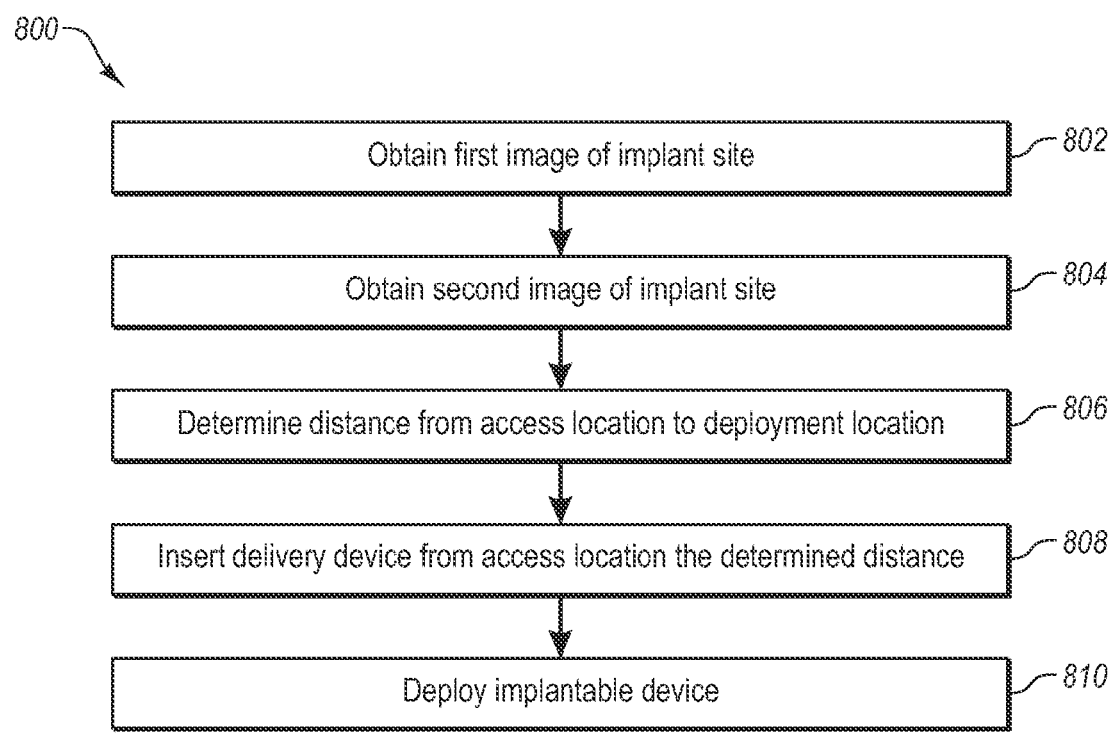
FIG. 8 illustrates another embodiment of a method for imaging an implant site.

In some embodiments, the process may be generally reversed to retrieve a deployed implantable device. For example, a lumen filter, such as implantable device 520 shown in FIGS. 5A-5B, may be removed from the delivery location 544 and/or through the access location (shown as 142, 242, 342 in FIGS. 1-3). The determined distance may provide sufficient information for the technician to retrieve the implantable device FIG. 8 illustrates another embodiment of a method 800 for imaging an implant site. In the present embodiment, the method 800 may be used in conjunction with the imaging device 401 and components described in connection with FIG. 4, the implantable device 520, 620 and other system components described in connection with FIGS. 5A-5B and 6, and/or any other systems and/or apparatus for imaging an implantable device and/or incorporated described herein. The method 800 of this other embodiment may be functionally similar to that of the method 700 previously described above and shown in FIG. 7 in most respects, wherein certain features will not be described in relation to this other embodiment wherein those method components may be performed in the manner as described above and are hereby incorporated into this alternative embodiment described below.

The method 800 may include obtaining a first image of the implant site, as represented by block 802. The patient may be positioned with respect to the imaging device. For example, the patient may be positioned based on a desired image orientation. The first image may be obtained using various imaging devices. The images of this embodiment may be functionally similar to the images 102, 202, 302 previously described above and shown in FIGS. 1-3 in most respects, wherein certain features will not be described in relation to this embodiment wherein those components may function in the manner as described above and are hereby incorporated into this alternative embodiment described below. The patient may be repositioned.

A second image of the implant site may be obtained, as represented by block 804. The second image may be obtained using various imaging devices. The second image may be different from the first image. For instance, the first image may be similar to the image 100 described in connection with FIG. 1 and the second image may be similar to the image 200 described in connection with FIG. 2. In another example, the first image may be similar to the image 200 described in connection with FIG. 2 and the second image may be similar to the image 300 described in connection with FIG. 3. Other combinations of images may be used.

In the present embodiment, a first image and a second image may be obtained. In other embodiments, a first, second, third, and/or more images may be obtained. In further embodiments, only a first image may be obtained.

A distance from an access location to a deployment location may be determined, as represented by block 806. The distance may be determined by a technician, the imaging device, and/or other determiners. The distance may be an approximate distance. The distance may be determined based on information provided by the first image, second image, and/or other images of the implant site.

In one example, a technician may inspect the first image (i.e. a frontal projection) and the second image (i.e. a lateral projection) of the implant site to determine an approximate distance. The technician may determine a first distance (i.e. a longitudinal or vertical distance in a z-axis direction) from the first image and a first distance (i.e. a longitudinal or vertical distance in a z-axis direction) from the second image to determine an average first distance. The technician may determine a second distance (i.e. a lateral distance, such as a width, in an x-axis direction) from the first image and a third distance (i.e. a lateral distance, such as a depth, in a y-axis direction) from the second image. The first, second, and/or third distances may be used to determine an approximate total distance from the access location to the deployment location. For example, the average vertical (i.e. longitudinal) distance, the second distance, and/or the third distance may be used to determine an overall approximate distance from the access location to the deployment location.

In another example, the imaging device may inspect the first image (i.e. a frontal projection) and the second image (i.e. a cranial projection) of the implant site to determine an approximate distance. The imaging device may determine a first distance (i.e. a longitudinal or vertical distance in a z-axis direction) from the first image. The imaging device may determine a second distance (i.e. a lateral distance, such as a width, in an x-axis direction) from the first image and a second distance (i.e. a lateral distance, such as a width, in an x-axis direction) from the second image to determine an average horizontal distance. The imaging device may determine a third distance (i.e. a lateral distance, such as a depth, in a y-axis direction) from the second image. The first, second, and/or third distances may be used to determine an approximate total distance from the access location to the deployment location. For example, the first distance, the average horizontal distance, and/or the third distance may be used to determine an overall approximate distance from the access location to the deployment location.

Some distances may carry more weight than others. For example, in the images 102, 202, 302 shown in FIGS. 1-3, the first distance 130*a*, 230*a* may be larger than the second or third distances, 130*b*, 330*b*, 230*c*, 330*c*, respectfully. This may be due to the patient's vasculature. For example, the inferior vena cava may have a larger longitudinal component than any lateral components. The distances may be weighted based on similar factors such as known and/or predicted differences between the various distances.

In another example, the imaging device may interpret data from the first and/or second image of the implant site to determine an approximate distance. The determined distance may be used to approximate a distance that a delivery device to deliver an implantable device near a delivery location might travel.

A delivery device may be inserted from the access location the determined distance, as represented by block 808. The delivery device may be marked with the determined distance, such that the technician may know when the implantable device is near the delivery location. The delivery device may be marked with a measuring scale that the technician may use to determine when the implantable device is near the delivery location. The implantable device may be deployed, as represented by block 810.

After the implantable device has deployed, the location of the implantable device may be verified. For instance, where the imaging device used to obtain an image uses projectional radiography, the location of the implantable device may be verified by a fluoroscope. In another example, the location of the implantable device may be verified by an ultrasonic imaging device.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

I claim:

1. A method for delivering an embolic filter to an embolic filter site within a body lumen, comprising:
    positioning a patient relative to a plain film radiographic, non-fluoroscopic imaging device;
    obtaining a first image of the embolic filter site using the plain film radiographic, non-fluoroscopic imaging device;
    determining a distance from an access location at an exterior location of the patient to a deployment location at an interior location of the patient;
    after determining the distance from the access location to the deployment location, inserting a delivery device from the access location at an exterior location the determined distance; and
    deploying the embolic filter.

2. The method of claim 1, wherein the delivery device includes at least one distance mark.

3. The method of claim 2, wherein the determined distance is indicated by the at least one distance mark.

4. The method of claim 1, further comprising verifying a deployed location of the implantable device.

5. The method of claim 4, wherein the deployed location of the implantable device is verified using fluoroscopy.

6. The method of claim 4, wherein the deployed location of the implantable device is verified using ultrasonic imaging.

7. The method of claim 1, wherein the delivery device is a catheter.

8. A method for preparation of an embolic filter site within a body lumen for an embolic filter, comprising:
    positioning a patient relative to a plain film radiographic, non-fluoroscopic imaging device;
    obtaining a first image of the embolic filter site using the plain film radiographic, non-fluoroscopic imaging device; and
    prior to inserting a delivery device into the patient, determining a distance from an access location at an exterior location of the patient to a deployment location at an interior location of the patient, the distance being along the length of the body lumen, the access location being remote from the deployment location.

9. The method of claim 8, further comprising obtaining a second image of the embolic filter site.

10. The method of claim 9, wherein a plane of the first image and a plane of the second image are separated by an angle.

11. The method of claim 10, wherein the plane of the first image and the plane of the second image are parallel to a vertical axis through a patient.

12. The method of claim 9, wherein determining the distance from an access location to a deployment location further comprises measuring a first distance from the first image, measuring a second distance from the second image, and determining an approximate total distance from the access location to the deployment location along the body lumen using the first distance and the second distance.

13. The method of claim 12, wherein the approximate total distance is accurate within about one inch.

14. The method of claim 9, further comprising obtaining a third image of the implant site.

15. The method of claim 14, wherein a plane of the first image and a plane of the second image are separated by a first angle and the plane of the first image and a plane of the third image are separated by a second angle.

16. The method of claim 8, wherein determining the distance from an access location to a deployment location further comprises measuring a first distance from the first image and determining an approximate total distance from the access location to the deployment location using the first distance.

17. The method of claim 8, wherein the embolic filter is a vena cava filter.

18. A method for delivering an embolic filter to an embolic filter site within a blood vessel, comprising:
    positioning a patient relative to a plain film radiographic, non-fluoroscopic imaging device;
    obtaining a first image of the embolic filter site using the plain film radiographic, non-fluoroscopic imaging device;
    obtaining a second image of the embolic filter site using the plain film radiographic, non-fluoroscopic imaging device, the second image being oriented substantially perpendicular to the first image;
    measuring a first vertical distance from an access location in a femoral artery of the patient to a deployment location in a vena cava of the patient from the first image;
    measuring a first horizontal distance from the access location in the femoral artery of the patient to the deployment location in the vena cava of the patient from the first image;
    measuring a second vertical distance from the access location in the femoral artery of the patient to the deployment location in the vena cava of the patient from the second image; and
    measuring a second horizontal distance from the access location in the femoral artery of the patient to the deployment location in the vena cava of the patient from the first image;
    determining an approximate total distance from the access location in the femoral artery of the patient to the deployment location in the vena cava of the patient along the length of the blood vessel using the first vertical distance, the second vertical distance, the first horizontal distance, and the second horizontal distance;
    inserting a delivery device from the access location in the femoral artery of the patient the determined approximate total distance; and
    deploying the embolic filter.

* * * * *